United States Patent
Torino et al.

(10) Patent No.: US 11,311,853 B2
(45) Date of Patent: Apr. 26, 2022

(54) PROCESS FOR THE PREPARATION OF DOUBLE CROSSLINKED CORE-SHELL POLYMERIC NANOPARTICLES FOR MULTIMODAL IMAGING AND THERANOSTIC APPLICATIONS

(71) Applicant: FONDAZIONE ISTITUTO ITALIANO DI TECNOLOGIA, Genoa (IT)

(72) Inventors: Enza Torino, Naples (IT); Paolo Netti, Naples (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 0 days.

(21) Appl. No.: 16/487,896

(22) PCT Filed: Feb. 22, 2018

(86) PCT No.: PCT/IB2018/051087
§ 371 (c)(1),
(2) Date: Aug. 22, 2019

(87) PCT Pub. No.: WO2018/154470
PCT Pub. Date: Aug. 30, 2018

(65) Prior Publication Data
US 2019/0381471 A1    Dec. 19, 2019

(30) Foreign Application Priority Data
Feb. 23, 2017    (IT) .................. 102017000020707

(51) Int. Cl.
| | |
|---|---|
| *B01J 13/10* | (2006.01) |
| *A61K 49/00* | (2006.01) |
| *A61K 51/04* | (2006.01) |
| *A61K 51/12* | (2006.01) |
| *C08L 5/08* | (2006.01) |
| *C08L 67/03* | (2006.01) |
| *C08L 77/04* | (2006.01) |
| *C08L 89/00* | (2006.01) |
| *B82Y 5/00* | (2011.01) |

(52) U.S. Cl.
CPC ........... *B01J 13/10* (2013.01); *A61K 49/0093* (2013.01); *A61K 51/0491* (2013.01); *A61K 51/1244* (2013.01); *C08L 5/08* (2013.01); *C08L 67/03* (2013.01); *C08L 77/04* (2013.01); *C08L 89/00* (2013.01); *B82Y 5/00* (2013.01); *C08L 2205/22* (2013.01); *C08L 2207/53* (2013.01); *C08L 2312/00* (2013.01)

(58) Field of Classification Search
None
See application file for complete search history.

(56) References Cited

PUBLICATIONS

Courant T. et al., "Hydrogels incorporating GdDOTA: towards highly efficient dual T1/T2 MRI contrast agents", Angewandte Chemie International Editionn, Aug. 2, 2012, pp. 9119-9122.
Giridharan L.M., et al., "A rationally designed photo-chemo core-shell naomedicine for inhibiting the migration of metastatic breast cancer cells followed by photodynamic killing",Nanomedicine: Nanotechnology, Biology and Medicine 10 (2014) 579-587.
Russo M., et al., "A microfluidic platform to design crosslinked hyluronic acid nanoparticles (cHANPs) for enhanced MRI", Scientific Reports, vol. 6, No. 1, Nov. 30, 2016.
Search Report and Written Opinion of PCT/IB2015/051087 dated May 16, 2018.
Zhang L., et al., "Hyaluronic acid-chitosan nanoparticles to deliver Gd-DTPA for MR Cancer Imaging", Nanomaterials, 2015, 5, 1379-1396.

*Primary Examiner* — Jennifer Lamberski
(74) *Attorney, Agent, or Firm* — Silvia Salvadori, P.C.; Silvia Salvadori

(57) ABSTRACT

The present disclosure relates to a process for the preparation of core-shell particles by the coacervation method encapsulating contrast agents for multimodal imaging. The process consists in: a. Providing a water in oil emulsion of a biocompatible polyelectrolyte polymer. b. Providing an aqueous solution of a biocompatible polyelectrolyte polymer having opposite charges of the polyelectrolyte of step a). c. Adding a crosslinking agent to the primary emulsion and the secondary solution. d. Adding at least a tracer independently to the primary emulsion or the secondary solution or emulsion. e. Adding the secondary aqueous solution to the primary emulsions and occurring of the complex coacervation leading to the separation of the coacervate particles. f. Optionally absorb a further tracer into the nanoparticles The disclosure also relates to the coacervates obtained by the above described process and their use as probe for multimodal imaging in the diagnostic field.

7 Claims, 12 Drawing Sheets

PROCESS FOR THE PREPARATION OF DOUBLE CROSSLINKED CORE-SHELL POLYMERIC NANOPARTICLES FOR MULTIMODAL IMAGING AND THERANOSTIC APPLICATIONS

This application is a U.S. national stage of PCT/IB2018/051087 filed on 22 Feb. 2018 which claims priority to and the benefit of Italian patent application No. 102017000020707 filed on 23 Feb. 2017, the content of which are incorporated herein by reference in their entireties.

TECHNICAL FIELD

The present invention relates to the field of probes, radiotracers and contrast agents for medical imaging, in particular for the emerging multimodal imaging techniques.

BACKGROUND

The field of multimodal imaging has seen rapid progress in the last decade, thanks to its value demonstrated in numerous studies. Multimodal imaging allows integration of the strengths of individual modalities while overcoming their limitations. For instance, anatomical imaging technologies, such as Magnetic Resonance Imaging (MRI), provide unparalleled structural detail; whereas functional modalities such as Positron Emission Tomography (PET) provide insight into morphological and functional behaviours. The recent emergence of "hybrid" imaging devices combining MRI and PET modalities enables two diagnostic tests to be performed on the same system simultaneously, thereby avoiding multiple tests and improving registration performance, all of which prove useful for planning radiation therapy.

Recent developments in multimodal imaging have led to hybrid diagnostic equipment such as PET-MRI, Single-Photon Emission Computer Tomography-Magnetic Resonance Imaging (SPECT-MRI) and optical PET, which have paved the way for implementation of multimodal imaging protocols.

In parallel with the appearance of these "hybrid" tools, the need of new probes and radiotracers has arisen and nanotechnology is now playing a key role in the preparation of new probes that can be used for multimodal applications.

In particular, complex coacervation, which is a unique type of electrostatically-driven liquid-liquid phase separation from association of oppositely charged macro-ions, is an interesting preparation process because it is considered scalable and low-cost. Furthermore, another great advantage of this process is the production of high payload (up to 99%) nanostructures with controlled release properties.

The main disadvantage of the coacervation process is the high number of involved parameters and this complexity has attracted the interest of several studies on the stability of coacervates, in particular of those made of biocompatible polymers. For example, in EP1163274B9 the formation of hyaluronic acid-chitosan coacervates is reported as by-products of a process for the preparation of multiple cross-linked hyaluronic acid films and gels. Kaimatzer et al. in Soft Matter, (2015), 11, 8605 investigated the effects of pH, ionic strength, charge density, chain length and charge ratio on the synthesis of unloaded hyaluronic acid-chitosan coacervates.

Nowadays, complex coacervation processes are widely employed for micro-production in processed food, cosmetics, paper and textiles, in addition to their use in the pharmaceutical and nutraceutical field. For example, Liu et al. in J Mater Sci: Mater Med (2007) 18:2215-2224 reported a coacervation process for the preparation of chitosan-hyaluronate double-walled particles and their use as carriers for protein drugs.

Conversely, in the field of diagnostic imaging, especially for MRI, the use of the coacervation process has been limited so far by the difficulties in combining stable nanostructures and contrast agents. Indeed, the conjugation of contrast agents to the encapsulating polymer needs a tradeoff between the stability of the coacervate and the use of not completely biocompatible materials for MRI applications. An attempt in this direction is reported by Wang et al. in Chem. Commun., 2013, 49, 3736 wherein lanthanide ions, namely europium (III) and gadolinium (III), were encapsulated in a 20 nm radius coacervate micellar structure in a controlled way. The encapsulating materials are the ligand 1,11-bis(2,6-dicarboxypyridin-4-yloxy)-3,6,9-trioxaundecane (also named $L_2EO_4$) and the di-block copolymer poly (N-methyl-2-vinyl-pyridinium iodide)-b-poly(ethylene oxide) (also named $P2MVP_{41}$-b-$PEO_{205}$). The as obtained micelles showed a magnetic relaxation in the same order observed with other micelle systems.

Nonetheless, the biocompatibility of coacervates and their ability of stably encapsulate contrast agents thus avoiding the risk of undesired release inside the body still are crucial issues for the clinical approval of this new generation of probes and radiotracers for multimodal imaging techniques.

The present disclosure solves this long felt problem by providing a coacervation process which combines the presence of two crosslinking agents with a strict control of the complex coacervation conditions of biocompatible polymers during the phase separation step, thus leading to stable and biocompatible coacervates encapsulating multimodal contrast agents.

SUMMARY OF THE INVENTION

The present disclosure relates to a process for the preparation of coacervate nanoparticles made of biocompatible polymers and stably encapsulating a contrast agent for medical imaging. The disclosure also relates to coacervate particles made of biocompatible polymers loaded with at least a contrast agent or a radiotracer and to their use in vivo image diagnostic methods.

DETAILED DESCRIPTION

Figure 1:
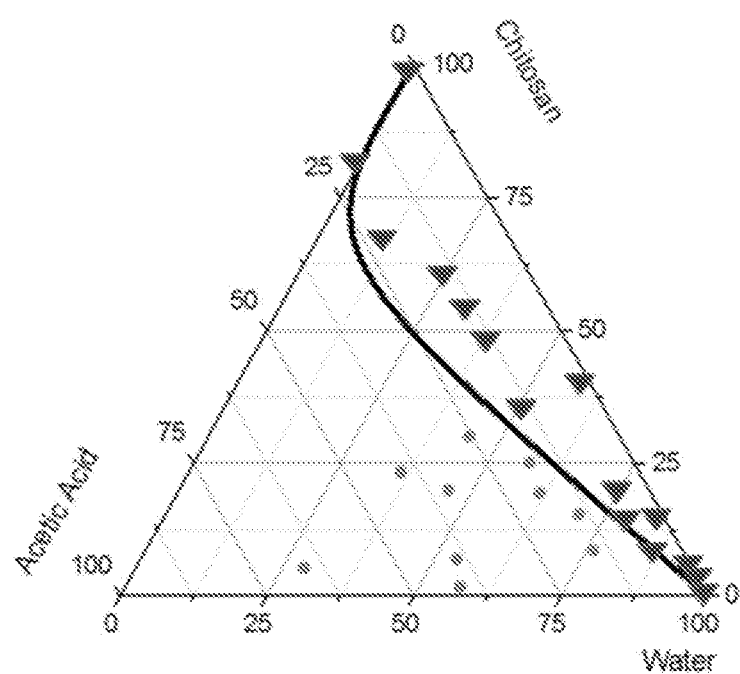
FIG. 1 shows the experimental ternary diagram at room temperature for the water-acetic acid-chitosan system.

To the extent of the present disclosure, the following terms have to be intended with the here specified meaning:

"Polyelectrolyte polymer" is a polymer in which a substantial portion of the constitutional units have ionizable or ionic groups, or both.

The word "biocompatible" referred to a material, means that said material does not have toxic or injurious effects on the biological functions.

"Contrast agent" or "contrast medium" is a substance used to enhance the contrast of structures or fluids within the body in several medical imaging techniques.

"Radiotracer" is a chemical compound in which one or more atoms have been replaced by a radioisotope so by virtue of its radioactive decay it can be used in medical imaging to explore the mechanism of chemical reactions inside the living body by tracing the path that the radioisotope follows from reactants to products.

"Optical tracer" is a non-toxic molecules that can be visualized by using visible, ultraviolet, and infrared light.

"Coacervate" or "coacervate nanoparticle" means a particle obtained by electrostatically-driven liquid-liquid phase separation.

"MRI" is the acronym of Magnetic Resonance Imaging

"PET" is the acronym of Positron Emission Tomography

"Optical Imaging" refers to various imaging techniques that use visible, ultraviolet, and infrared light. Examples of optical imaging in medicine are Optical Coherence Tomography, Spectroscopy, Fluorescence microscope.

In a first aspect the present disclosure relates to a process for the preparation of loaded coacervate comprising the following steps:

a) Providing a water in oil emulsion of a biocompatible polyelectrolyte polymer.

b) Providing an aqueous solution of a biocompatible polyelectrolyte polymer having opposite charges of the polyelectrolyte of step a).

c) Adding two crosslinking agents, one to the emulsion and the other one to the aqueous solution.

d) Adding a contrast agent for medical imaging to the emulsion and/or to the solution.

e) Adding the aqueous solution to the emulsion at a constant temperature comprised between 19 and 37° C. and at a pH comprised between 3 and 7, thus obtaining the separation of the coacervate particles.

f) Optionally adding a further optical tracer, radiotracer or contrast agent for medical imaging to the coacervate particles obtained in step e).

In step a) a water in oil (w/o) emulsion is prepared by first dissolving a biocompatible polyelectrolyte polymer, having a concentration ranging from 0.1% to 1% wt/v, in an aqueous solution and then mixing the obtained solution with an oil phase. Said oil phase is obtained by dissolving a surfactant, such as for example Span 80, Span 20, CTAB, SDS, Tween 20, Tween 80, Brij93 and Poloxamers, in an oil such as mineral oil, Silicon Oil, Chlorinated Paraffin Oil, Cotton Seed Oil, Vegetable Oil, Animal Oil, Triglyceride Oil, a combination thereof and similar products, and homogenizing the whole mixture. In a preferred embodiment said first biocompatible polyelectrolyte polymer is selected from the group consisting of poly(L-lysine), chitosan, bovine serum albumin (BSA), Human Serum Albumin, Poly Lactic-co-Glycolic Acid (PLGA) Poly Lactic-co-Glycolic Acid-PolyethyleneGlycol (PLGA-PEG) di and tri-block, Poly Lactic Acid (PLA) and Poly Lactic Acid-PolyethyleneGlycol (PLA-PEG) tri and Di-block, cellulose derivatives such as chitosan-carboxymethyl cellulose (CMC), n-alginate, hydroxypropyl methyl cellulose (HPMC), dextran derivatives such as Poly(N-isopropylacrylamide) (PNIPAAm) and Poly(N-vinylcaprolactam)-hydroxyethylmethacrylate (PVCL-HEMA) grafted on dextran chain, methacrylated dextran (dex-MA) and hydroxyethyl-methacrylated dextran (dex-HEMA), glycidyl methacrylated dextran (dex-GMA), poly (vinylbenzyl trialkyl ammonium), Poly (4-vinyl-N-alkyl-pyridinium), poly (acryloyl-oxyalkyl-trialkyl ammonium), poly (acryamidoalkyl-trialkyl ammonium), poly (diallydimethyl-ammonium), Poly(N-isopropylacrylamide) (PNIPAAm), poly-(hydroxyethylmethacrylate) poly HEMA and maleic acid/diallylamine copolymer. In a further preferred embodiment, the first biocompatible polyelectrolyte polymer is chitosan or bovine serum albumin (BSA).

In step b) an aqueous solution of a second biocompatible polyelectrolyte having opposite charges with respect the polyelectrolyte of step a) is prepared in a concentration range comprised between 0.01 and 1% wt/v. In a preferred embodiment said second biocompatible polyelectrolyte polymer is selected from the group consisting of hyaluronic acid, poly(L-glutamic acid), carraggenan, alginates, pectin, chitin, cellulose derivatives, starch derivatives, dextran derivatives, poly (styrenesulfonic acid), poly (vinylsulfonic acid), poly (acrylic or methacrylic acid), poly (itaconic acid), maleic acid/diallyamine copolymer and chitosan. In a further preferred embodiment, the first biocompatible polyelectrolyte polymer is hyaluronic acid or chitosan.

In step c) a crosslinking agent in a concentration range between 5 and 60% v/v is added to the emulsion and another crosslinking agent is added to the solution. In a preferred embodiment, the crosslinking agent is a biocompatible crosslinking agent. Preferably, Divinyl Sulfone (DVS) is used as first crosslinking agent and TriPolyPhosphate (TPP) as second. The person skilled in the art would recognise suitable biocompatible crosslinking agents for the emulsion or the solution, on the basis of known chemical compatibilities, without undue experimentation In step d), the contrast agent can be added to the emulsion and/or to the solution on the basis of the chemical compatibility with the substances employed up to this step. Suitable contrast agents are selected from the group consisting of Gd-diethylenetriaminepentacetate (Gd-DTPA), gadolinium-diethylenetriaminepentaacetic acid (Gd-DOTA), Gadoterate, Gadodiamide, Gadobenate, Gadoteridol, Gadofosveset and Gadoversetamide, Fluorine-19.

In a preferred embodiment, the MRI contrast agent is Gd-DTPA or Gd-DOTA or Fluorine-19.

Step e) is carried out at strictly controlled pH and the temperature values, respectively kept in the range of 3 and 7 and 19° C. and 37° C. After the addition of the solution phase to the emulsion, coacervation starts as soon as the polyelectrolyte molecules of the solution reach the surface of the droplets contained in the emulsion. The reaction is kept under stirring at a selected constant temperature until a phase separation spontaneously occurs. Preferably:

- if the process is performed at a constant temperature value comprised in the range from 19 to 27° C., the coacervation will continue at the same isothermic temperature until a complete coacervation occurs;
- otherwise, if the process is performed at higher temperature, i.e. above 27° C. (for instance at 35° C.), as soon as the coacervation starts the solution is rapidly cooled to a temperature comprised between 19 and 25° C. In a preferred embodiment, a temperature of 23° C. is used to perform an isothermic coacervation, while if the process is performed at 35° C. then the solution is rapidly cooled to 25° C. at a rate of about 5° C./h.

Finally, the as obtained nanocoacervates are preferably dialysed and ultracentrifugated.

Step f) allows adding other contrast agents to the coacervate particles obtained in step e), such as fluorophores for optical imaging and/or radiopharmaceutical substances for PET or scintigraphy, in addition to contrast agents for MRI encapsulated in step d). Step f) is carried out by common addition techniques such as absorption, adsorption, solvent evaporation, solvent displacement, freeze drying, supercritical carbon dioxide techniques, phase separation, mixing. The as obtained final product coacervate particles loaded with several contrast agents for multimodal imaging. Suitable radiotracer for PET are for example Fludeoxyglucose (FDG) and radioactive technetium (Tc99m-MAA). Suitable contrast agents for fluorescence optical imaging, are for example Indocyanine Green (ICG) and other commercially available optical tracers such as nt (BLZ-100), CLR1501 CLR1502, OTL38, cRGD-ZW800-1, YC-27, PSMA-1-IR800, Fluorocoxib A, BMV109, LUM105, MMP-2-sensitive NIRF probe, Z-Phe-Arg-HMRG, Lipidated probe 3, 6QCNIR, RACPP AVB-620 and C-SNAF. Preferably the contrast agent for fluorescence optical imaging is Indocyanine Green.

In a preferred embodiment, trimodal imaging capability is obtained by: Gd-DTPA contrast agent for MRI, Fludeoxyglucose (FDG) radiotracer for PET and Indocyanine Green (ICG) for optical imaging. All these compounds are employed without any chemical modification, thus preserving the FDA approved formulation.

In a preferred embodiment, the above described process is carried out by using chitosan as biocompatible polymer for the emulsion and hyaluronic acid (HA) as biocompatible polymer for the solution. A hyaluronic acid having a molecular weight ratio up to of 100:0.1 with respect to chitosan is preferably employed. It means that, for example, if chitosan is 30 000 Da, a preferred HA could be 90 000 Da. The choice of hyaluronic acid with a higher molecular weight with respect to the molecular weight of chitosan, allows the complete coating of the chitosan nanodroplets. In this embodiment, divynil sulfone (DVS) and triphosphate (TPP) are used as crosslinking agents in order to create the double crosslinking in the final coacervates: an external one between the chains of hyaluronic acid and an internal one between the chains of hyaluronic acid and the chains of chitosan.

The above described process and, in particular the strict control over the coacervation conditions in step e), allows an improved stability of the final loaded coacervates and a reduction of the entire duration of the process. Indeed the inventors found that, thanks to temperature monitoring, a process time reduction from 24 hours to just 6.5-7 hours can be achieved. Furthermore, this process can be easily optimized and scaled up to a low cost industrial process, thanks to the availability of industrial monitoring technologies for parameters such as the concentration of the two polymers, the percentage of surfactants, the pH, the temperature and the duration of the different steps of the process.

In a further aspect, the present disclosure relates to core-shell coacervate particles stably encapsulating a contrast agent and optionally further including at least another contrast agent (e.g. a radiotracer or fluorophore molecule) for medical imaging. In a preferred embodiment, the coacervate particles of the present disclosure encapsulate a MRI contrast agent, a fluorophore molecule and a radiotracer. Preferably said MRI contrast agent is Gd-DTPA, said fluorophore agent is a cyanine dye or Fluorescein Isothiocyanate (ICG) and said radiotracer is Fludeoxyglucose (FDG).

The coacervate particles of the present disclosure preferably have a size comprised between 40 and 500 nm, further preferably between 40 and 70 nm.

The here disclosed coacervate particles, obtained by the cooling step, are extremely stable in water and do not show a swelling behaviour typical of prior art coacervates, as it can be seen from comparative example 5 of this specification, even at different pH values, as shown in example 11.

On the contrary, nanoparticles obtained at an isothermal temperature ranged between 22 and 27° C. show a pH-sensitive behaviour at pH 4-4.5.

This characteristic pH behavior may provide significant advances in the use of the disclosed coacervate nanoparticles as vectors for the diagnosis and treatment of tumor pathologies, for example in the emerging field of theranostic particles. In fact, the tumor environment, besides being devoid of oxygen, is also characterized by an acid pH and an impaired drainage ability of the lymphatic system. Hence the pH behavior of any vector is a key parameter to preview its behavior in the tumor microenvironment and, therefore, to achieve a better diagnosis and/or therapy.

Figure 8:
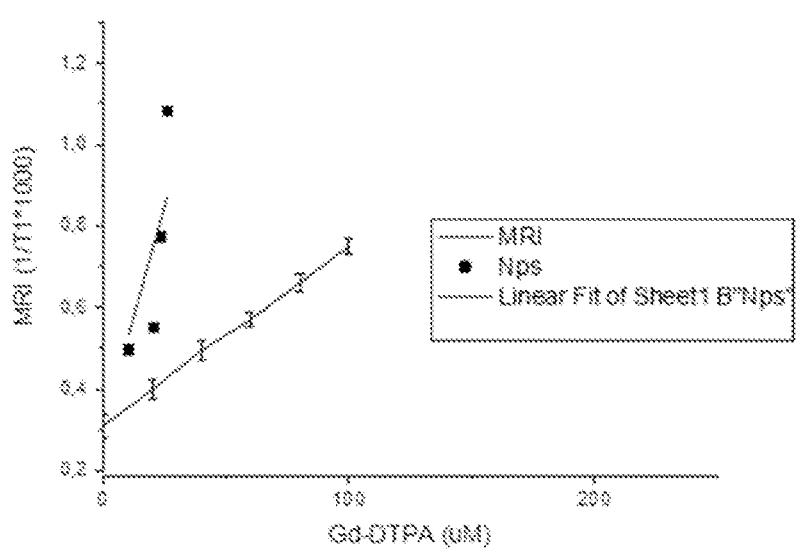
FIG. 8 is a graph reporting the relaxometric properties as a function of contrast agent (Gd-DTPA) concentration.

Furthermore, the here disclosed coacervate particles shows an average enhanced relaxivity in MRI, up to 8 times higher than commercial Gd-DTPA (4 mM sec$^{-1}$), as shown in FIG. 8 This is mainly due to the complex equilibrium formed in the coacervate particles by the elastic stretches of polymer chains, water osmotic pressure and hydration degree able to boost the relaxivity (data not shown). From a theoretical point of view, said complex equilibrium can be summarized in a new concept named by the present inventors "hydrodenticity", which can be applied not only to coacervate particles, but also to other types of materials, such as hydrogels, polymeric films, etc. In particular, the present inventors found that hydrodenticity allows the formation of water compartments containing the encapsulated contrast agent. The water compartment is responsible for the improvement of the imaging performance of the nanoparticles of the invention.

Figure 12:
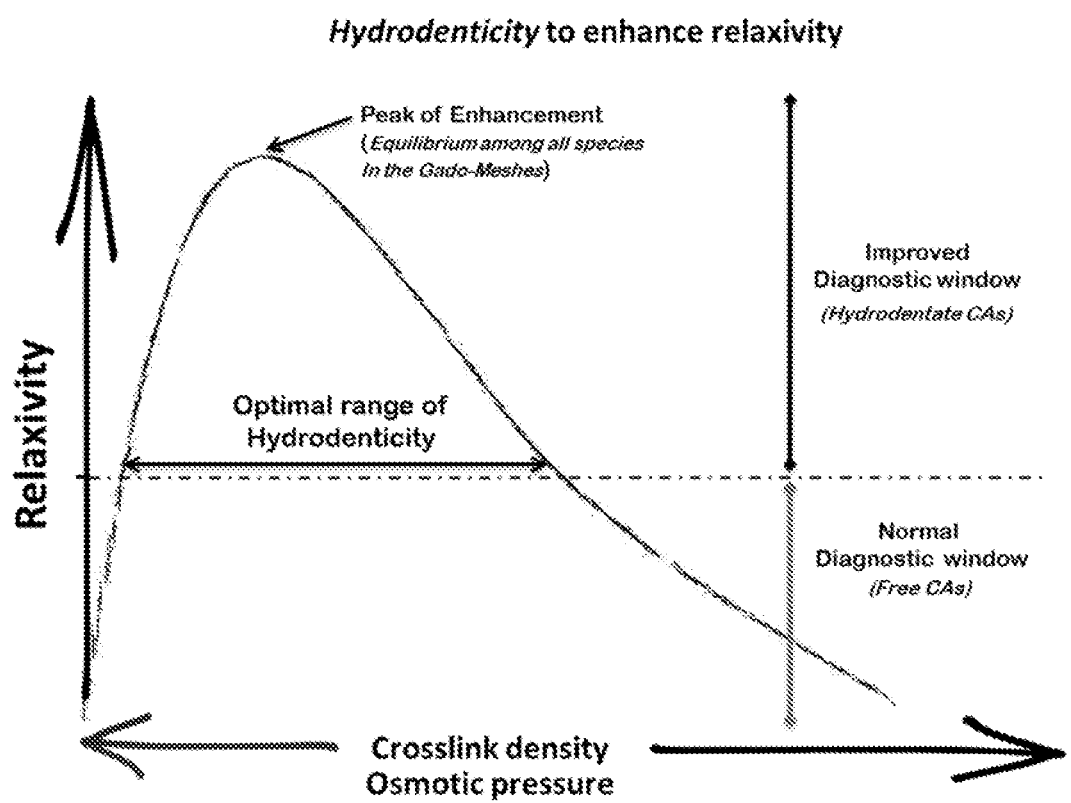
FIG. 12 shows a schematic qualitative illustration of an improved diagnostic window obtainable when using the coacervate nanoparticles encapsulating a contrast agent of the invention. The coacervate nanoparticles of the invention allows to overcome the limitations related to the use of commercial contrast agents such as low relaxivity, limited acquisition time and reduced tissue specificity.

Modulation of the hydrodenticity through: (i) elastic stretching of the polymer meshes (ii) osmotic pressure and (iii) hydrated state of the contrast agent (e.g. Gd-DTPA) allows obtaining customized nanoparticles for each pathology to be diagnosed. As a result it is possible to identify a customized diagnostic window for each pathology (for example shown in FIG. 12) by defining a range of optimal properties of the polymer matrix and the contrast agents. Such a customized diagnostic window improves efficacy in the treatment of a particular disease, thus avoiding toxic effects, and increasing the performance of the MRI acquisitions.

Additionally, it is worth noting that coacervates having size less than 70 nm, obtainable by the here disclosed process, may also be employed for controlled delivery of contrast agents to the brain.

Finally, in a further aspect, the present disclosure relates to the use of the above described coacervate particles as probe for multimodal imaging. The coacervate particles may advantageously be used in simultaneous PET/MRI imaging acquisition, preserving reduced toxicity, increased tissue specificity and higher sensitivity. Preferably, the coacervate particles of the present disclosure are used, after loading with the appropriate contrast agents, as single probe for trimodal imaging, in particular combining simultaneous MRI, PET and fluorescence imaging.

EXAMPLES

Example 1: Synthesis of Hyaluronic Acid-Chitosan Coacervates

The different materials that are used for nanoparticles production are: Chitosan (CHS) low molecular weight; Divinyl Sulfone (DVS) 118.15 g/mol; Sodium Tripolyphosphate (TPP) 367.86 g/mol; Glacial Acetic Acid molecular weight 60.05; Ethanol (EtOH) molecular weight 46.07; Gd-DTPA molecular weight 547.57; Mineral Oil 0.84 g/mL at 25° C. (lit.); Span80 molecular weight 274.43; 1.005 g/mL at 20° C. (lit.) are purchased by Sigma-Aldrich® while Hyaluronic Acid (HA) 850 kDa parenteral grade is by Hyasis®. MilliQ water is used for all experiments.

First, chitosan is solubilised in an aqueous solution in acid conditions. An aqueous solution of Chitosan and Acetic Acid (10-400 µl) was obtained by mixing 5 ml of MilliQ water at a chitosan concentration of 1% wt/v. The concentration of acetic acid is adjusted from 1.39 M to 0.034 M to balance the addition of Gd-DTPA at a concentration of 1.8 µM. Afterwards, the volume of acetic acid is added to balance the acid nature of Gd-DTPA to re-establish the pH conditions between 4.5 and 5. The oil phase is obtained by dissolving the surfactant Span 80 (0.5-1% wt/v) in 45 ml of Mineral Oil and homogenizing for 5 min at 7000 rpm. The as obtained primary emulsion is then treated for 20 minutes at 7000 rpm.

The secondary solution (coacervant phase), composed of 0.1% wt/v of hyaluronic acid in a water solution of 3 ml at 30% TPP (pH 10-11), is added dropwise to the w/o primary emulsion previously prepared and homogenized at 7000 rpm for 30 min, by controlling pH and temperature values at 4.5 and 35° C. respectively. The reaction is kept under stirring at room temperature until a phase separation spontaneously occurs. The final dispersion was homogenized at 7000 rpm for other 30 min, keeping the temperature at a constant value of 35° C. Afterwards, when the coacervation occurs, a cooling step is performed from 35° C. to 25° C. at about 5-10° C./h. Thereafter, 200 µl of the final solution are collected and diluted in 50 ml of EtOH, then filtered through an ISOPORE filter membrane of 100 nm and ultracentrifugated for 10 min at 15.000 rpm and 4° C. Thereafter nanoparticles were concentrated up to 10 mg/mL and adsorption of Glucose (simulating FDG) is performed. 100 microliter of a solution at 0.014 mg/mL of Glucose is added to the nanoparticles. The compounds are kept under stirring for 10 minute and then ultrafiltrated to remove the excess phase of Glucose. Adsorption of Glucose is 61% of the initial concentration.

The same procedure can be applied without performing a cooling step but at isothermal conditions, preferably at 23° C.

Example 2: Synthesis of Bovine Serum Albumin-Chitosan Coacervates

An aqueous solution of 0.3% wt/v of bovine serum albumin (BSA) in a water solution of 3 ml at pH 5-6 was prepared and an amount of 1.8 mM of Gd-DTPA was added. The oil phase was obtained by dissolving the surfactant Span 80 (0.5-1% wt/v) in 45 ml of Mineral Oil and homogenizing for 5 min at 7000 rpm. The as obtained primary emulsion was treated for 20 minutes at 7000 rpm.

The secondary solution (coacervant phase) of 0.1% wt/v chitosan in a water acid solution of 3 ml at pH 5-6 is prepared. The concentration of acetic acid is adjusted from 1.39 M to 0.034 M.

Then, the secondary solution, containing chitosan as coacervate polymer, is added dropwise into the primary water in oil emulsion previously prepared and homogenized at 7000 rpm for 30 minutes, by keeping the pH at constant values of 5-6. The reaction is kept under stirring over-night at 300 rpm at room temperature. The final dispersion it is homogenized at 7000 rpm for other 30 min, keeping the system at constant room temperature.

Example 3: Assessment of the Ternary Diagram at Room Temperature

The experimental assessment of the ternary diagram was made by varying the composition of the 3 compounds of example 1 at room temperature and analysing the behaviour of the final mixture. The experimental data are obtained from a solution obtained by mixing 1 ml of each of the 3 compounds. It has been found that, by adding the acetic acid dropwise, the gap between chitosan and water decreases, thus allowing the complete dissolution of the polymer into the acetic solution. The triangle working points represent concentrations at which the polymer is not dissolved into the solution (precipitation), while the circle working points represent the complete dissolution of the polymer. The line that drafts the gap of miscibility represents a transition line between the two different behaviours. The saturation of the system at 1% wt/v of chitosan is 2 µl/ml of the acetic acid solution.

Example 4: Process Optimization

Figure 2:
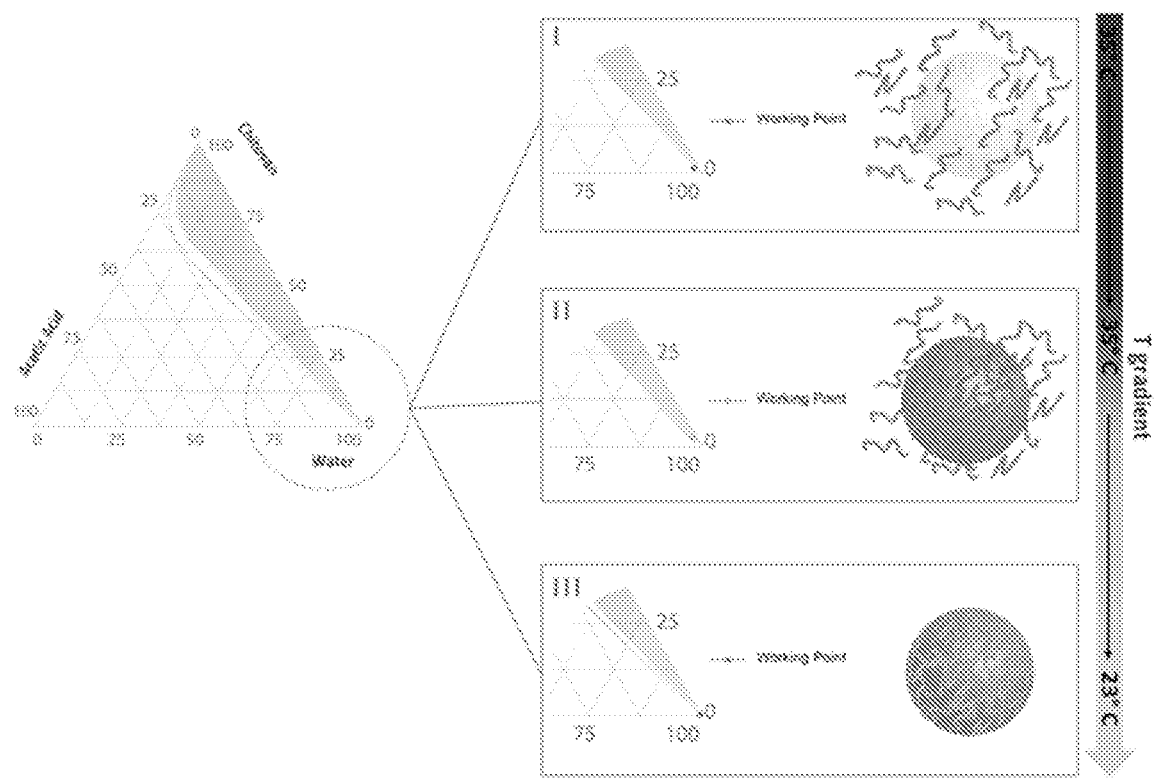
FIG. 2 is a scheme of the coacervation steps involved in this process.

As summarised in the scheme of FIG. 2, the main steps of the coacervation process in the light of ternary diagram, are the followings:

I. After the preparation of the primary w/o emulsion, the working point is located outside the miscibility gap that exists between water and chitosan. Therefore, there is still complete dissolution of the polymer into the solution of acetic acid;

II. Coacervation phase is added to the primary emulsion, promoting the dilution of the water phase; in this condition the concentration of the acetic acid solution decreases at 1.2 µl/ml thus going below the saturation limit. In the meantime, by keeping constant the temperature, acetic acid continues to evaporate inducing the shifting of the working point into the miscibility gap. This last step will lead to the formation of a chitosan template and to the coacervation of hyaluronic acid on it;

III. In the last phase, different isotherm conditions are evaluated in order to increase the coacervation step and to promote the stability of the nanoparticle's architecture. The inventors found that, thanks to temperature monitoring, a reduction from 24 h to 6.5-7 h of the duration time of the process is achieved.

Figure 3:
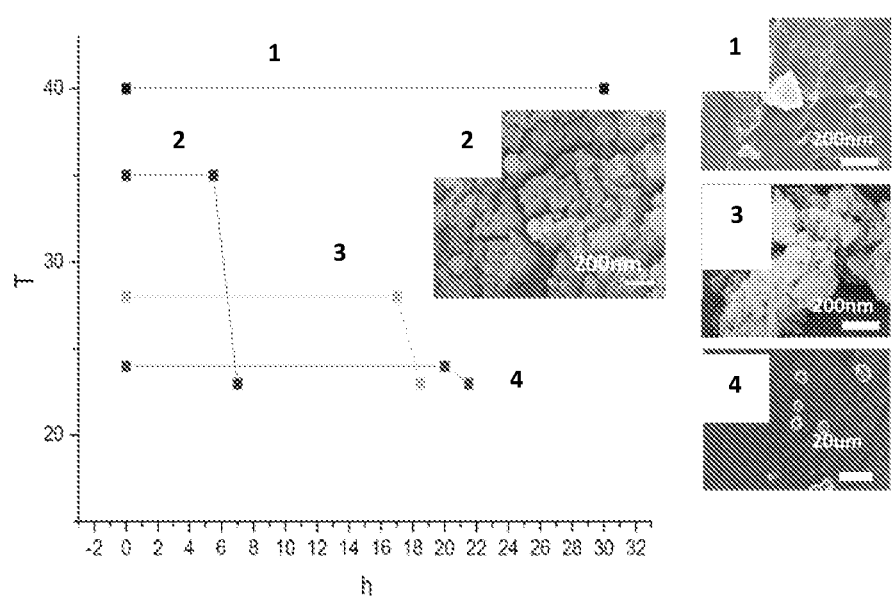
FIG. 3 shows a graph of the profile of demixing of the reaction at different gradients of temperature.

The variation of temperature that is used to speed up the process is an isothermal at 35° C. for 5.5 h and a ramp from 35° C. to 23° C. for 1.5 h (8° C./h) (reported in FIG. 3). After the isothermal step, the reaction of coacervation occurs and a demixing of the prepared solution is observed. After the demixing phase, a variation of the temperature should be suddenly performed to avoid aggregation phenomena and the destruction of the nanovectors. Indeed, as soon as the demixing phase occurs, the produced nanoparticles become unstable and a further drop in temperature is needed to increase the stability of the system.

Example 5: Comparative Example

Here are reported nanoparticles obtained according to a traditional coacervation process (employed coacervation conditions are 0.1% wt/v of HA, 1% wt/v of chitosan, 30% TPP wt/v and Gd-DTPA/Chitosan ratio 1:1) showing how the presence of Gd-DTPA leads to nanoparticles unstable in water, characterized by a swelling behaviour.

Figure 4:
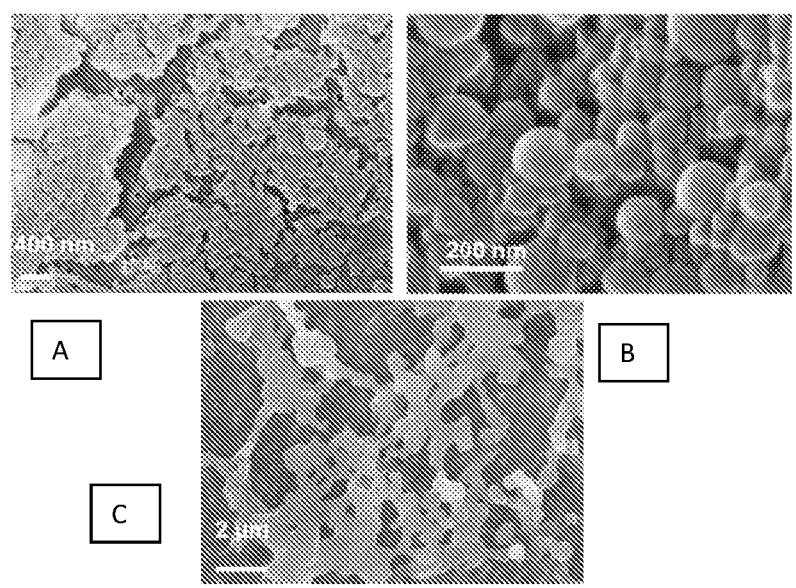
FIG. 4 shows in (A) and (B) stable nanoparticles collected in ethanol and in (C) unstable nanoparticles loaded with Gd-diethylenetriaminepentaacetic acid (Gd-DTPA) in water.

In FIG. 4(A) it is shown how the nanoparticles produced according to same coacervation method are stable in water in absence of Gd-DTPA and are unstable in presence of encapsulated Gd-DTPA. The outcomes clearly show that Gd-DTPA added to the solution compromises the stability and the morphology of the particles obtained according to the coacervation process with only one crosslinking agent. FIGS. 4 (A) and (B) are nanoparticles collected in ethanol and show how the coacervation process regularly occurs also in the presence of Gd. Figure (C) shows the instability of the nanoparticles when they are dissolved in water and obtained in the presence of Gd-DTPA, which interferes with the crosslinking.

Example 6: TEM Characterisation

Figure 5:
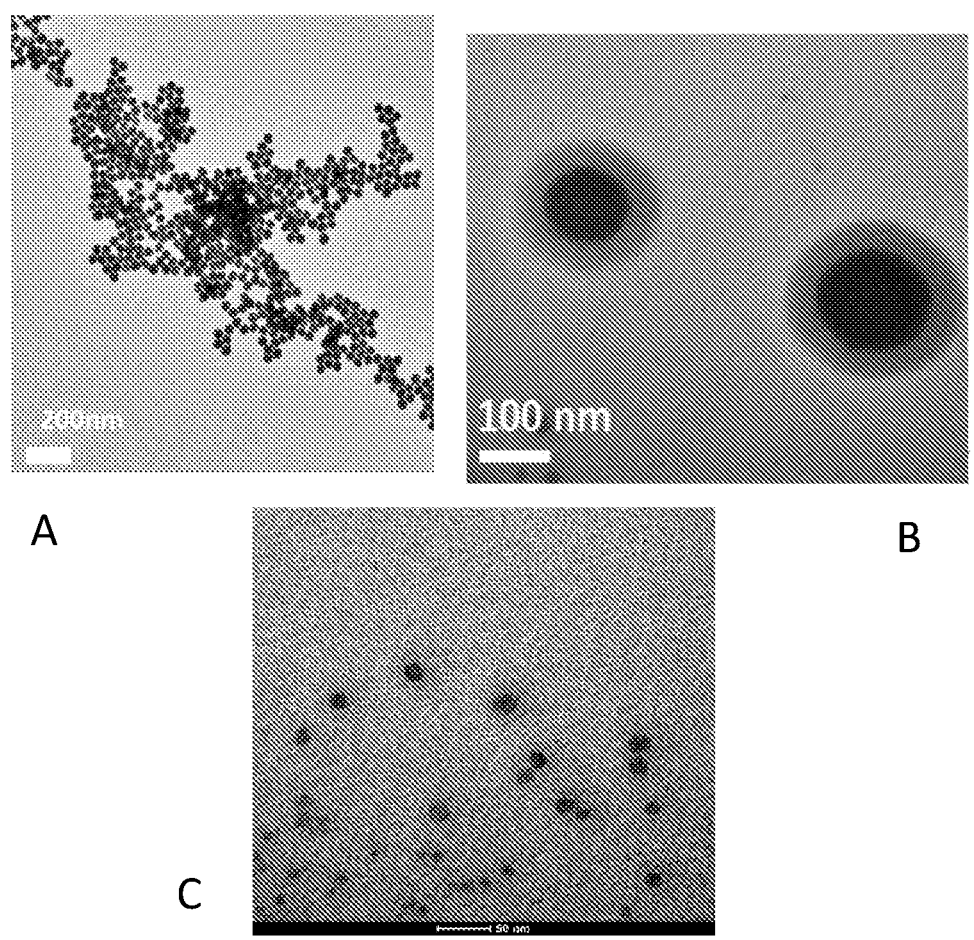
FIG. 5 shows magnifications of the same TEM image of the nanoparticles produced according to example 1: 200 nm (A), 100 nm (B) and 50 nm (C).

Transmission Electron Microscope (TEM) by FEI® in DRY, CRYO and Tomography (TOMO) modes, were carried out. In DRY mode the samples are prepared using Formvar/Carbon 200 mesh Cu Agar® depositing 20 μl of the suspended nanoparticles. In CRYO mode the samples are prepared using VITROBOT FEI® coating Lacey Carbon film 200 mesh Cu Agar® with 3 μl of nanoparticles suspension. The parameters of verification performed by VITROBOT are: blotting time of 1 s, humidity higher than 70% and temperature of 20° C. From the obtained images, a typical core-shell morphology can be seen. The results are shown in FIG. 5, wherein TEM images of the nanoparticles produced according to the here disclosed process at 1% wt/v of chitosan, 0.1% wt/v of hyaluronic acid and at room temperature with double crosslinking are reported.

Example 7: SEM Characterisation

Figure 6:
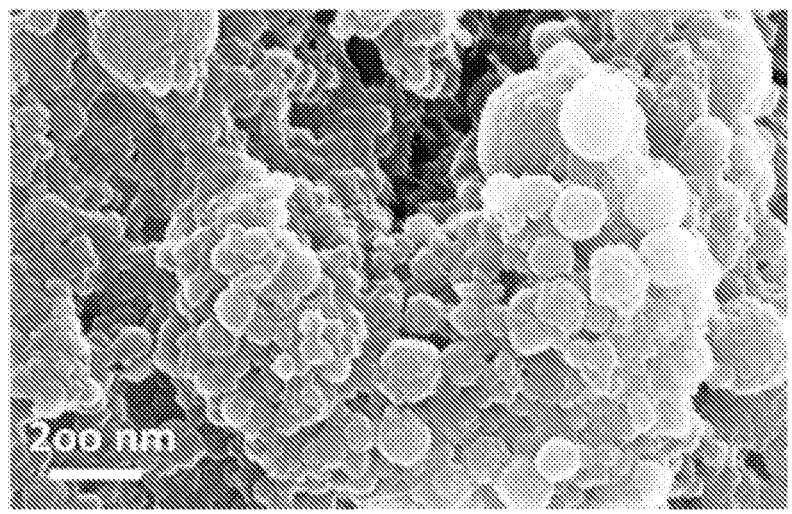
FIG. 6 shows a SEM image of the nanoparticles produced according to example 1, loaded with Gd-DTPA and after the sorption with a volume of Fludeoxyglucose (FDG) at 0.014 mg/ml.

A field emission scanning electron microscope (FE-SEM) by Zeiss® was used to investigate nanoparticles loaded with encapsulated Gd-DTPA and absorbed FDG. The sputter coating of the samples was made of 7 nm Au or PtPd. Mass spectrometry (MS) measures are made on eluate after a purification step of the particles. The results show a sorption of about 50% of the FDG after the contact of 10 min with the nanoparticles. FIG. 6 shows nanoparticles with Gd-DTPA after the sorption with a volume of FDG at 0.014 mg/ml and it can be seen how the particles morphology has not been compromised by the adsorption procedure.

Example 8: FT-IR Study

In order to investigate the linkage formation between chitosan, TPP and hyaluronic acid in the nanoparticles formation process of example 1, FT-IR studies were carried out. IR spectroscopy Thermo® was used and IR analysis were performed by measurements on raw powdered samples of Chitosan, hyaluronic acid and TPP while the treated samples are analyzed by deposition of 150 μl of nanoparticles suspension on silicon. The IR investigation proved the formation of interpolymer and intrapolymer crosslinking, thus confirming the hypothesis that the TPP bonds chitosan and hyaluronic acid (i.e. the core and the shell of the coacervate), whereas DVS bonds the hyaluronic acid chains and is responsible for stabilizing the core of the coacervate.

Figure 7:
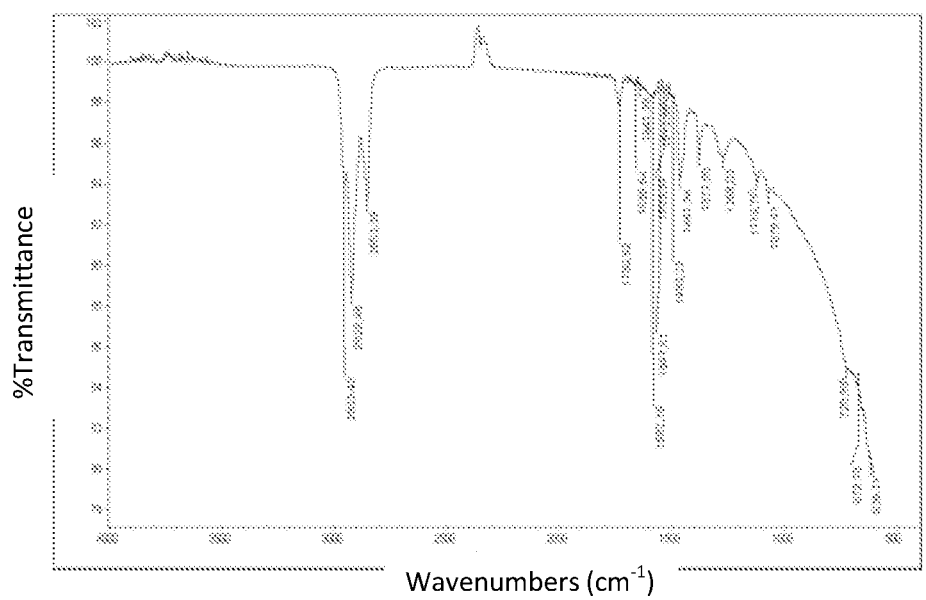
FIG. 7 is a FT-IR spectrum recorded on the coacervates obtained according to example 1.

In the interpretation of the IR spectrum, a band at 3450 $cm^{-1}$ can be attributed to the stretching of —$NH_2$ and —OH groups in the pure chitosan. In the IR spectrum of the obtained coacervates (see FIG. 7), these signals are not present, thus proving that the considered groups of chitosan reacted.

The two bands at 1658.64 $cm^{-1}$ and 1730.92 $cm^{-1}$ are assigned to the C=O stretching of hyaluronic acid.

The P=O (vibration absorption) peak at 1269 $cm^{-1}$ indicates the reaction between chitosan and tripolyphosphate. The peaks at 2953.42 $cm^{-1}$, 2922.48 $cm^{-1}$ and 2853.39 $cm^{-1}$ show the interactions of —CH groups.

Considering the signals of DVS, a peak at 1119.76 $cm^{-1}$ (S=O symmetric stretching vibrations) can be observed. After the DVS-hyaluronic acid reaction two peaks at 720.99 $cm^{-1}$ (S—C stretching vibrations) 1269 $cm^{-1}$ of the ether bond (C—O—C stretching vibrations) appears.

Example 9: Relaxometric Properties

Relaxometric properties are studied by Minispec 60 mq BRUKER® through the evaluation of the relaxation times T1 and T2. Experiments by Minispec 60 mq are made with glass tube on 300 μl of nanoparticles suspension. Free Induction Decay sequence (FID) is used to evaluate the best value of the Gain to control the saturation of the signal and measure T2*; Saturation Recovery (SR) and Inversion Recovery (IR) sequences are used to measure T1 instead Carr Purcell sequence (CPC) to evaluate T2. Concentrations of Gd-DTPA in the different nanostructures are evaluated by ICP-MS Agilent® to gain information about the loading capability of the produced nanocapsules.

Mass spectrometry (Agilent Technologies 6530 Accurate-Mass Q-TOF LC/MS) method is dedicated to the analysis of FDG. The mobile phase of elution system is chosen as acetonitrile (solvent A) and water (solvent B), with a flow rate of 10 μl/min and an injection volume of 10 μl. The used column is PLRP-S 100 A 3 μm 50×4 5 MM. Concentrations of Gd-DTPA in the different nanostructures are evaluated by ICP-MS Agilent®. Combining these data and the measures of relaxation times is possible to establish whether the method of production has led to the loading of the contrast agent (Gd-DTPA) but also to an increase of the signal due to the interaction of the contrast medium encapsulated with the water external to the carrier. The results show an enhancement of 12 times of the MRI signal $T_1$. The obtained results are reported in FIG. 12.

Example 10 Fluorescence Imaging

The obtained particles encapsulating an MRI contrast agent (Gd-DTPA) and different fluorescent agents were observed under fluorescent microscope (Stimulated Emission Depletion STED). Before the test, cyanine dye 5 (Cy5) (633 nm) was encapsulated into the nanoparticles. This dye was also useful for the optical imaging (Fluorescence Molecular Tomography, FMT) by Perkin Elmer.

Figure 9:
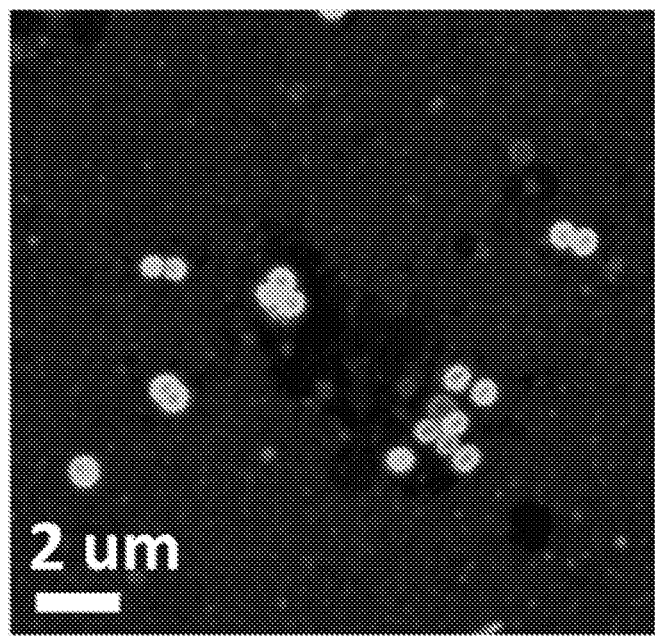
FIG. 9 shows a fluorescent microscope image of the nanoparticles are conjugated with Fluorescein Isothiocyanate (FITC) (488 nm) and are entrapping Gd-DTPA. In the image, it is possible to notice the difference between a core and a shell (white in the figure).
Figure 10:
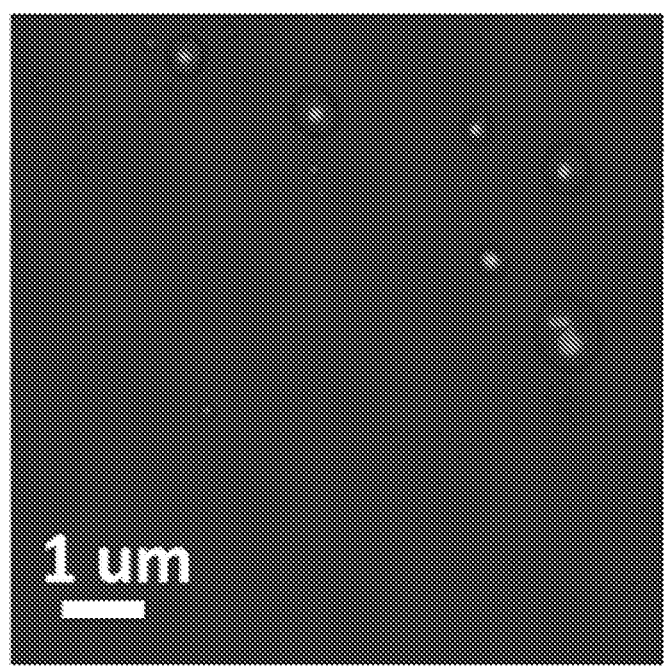
FIG. 10 shows a fluorescent microscope image of the nanoparticles wherein Gd-DTPA and a cyanine dye 5 (Cy5) (633 nm) are both encapsulated into the nanoparticles.
Figure 11:
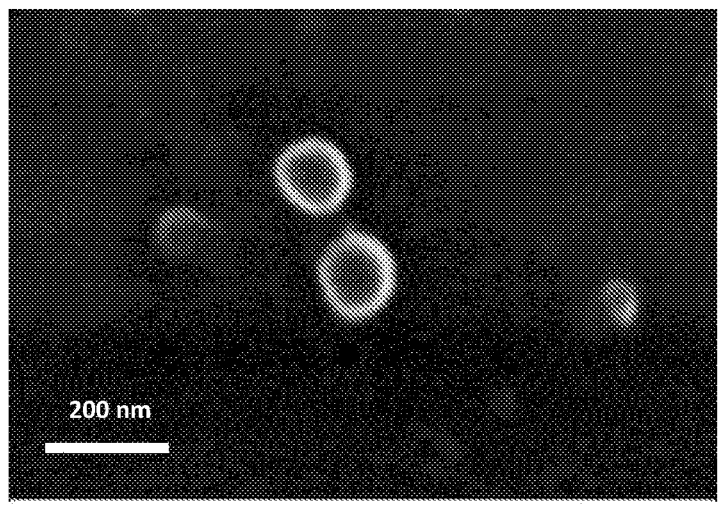
FIG. 11 shows a TEM image of the nanoparticles produced according to example 10.

In one case (FIG. 9) the image showed the shell as fluorescent part, whereas in FIG. 10 the whole nanoparticles appear fluorescent and there is not a difference between the two polymers apparently.

Example 11

Preliminary results on Hybrid Core-Shell (HyCoS) nanoparticles report a peculiar interesting pH-sensitive behavior of the nanovectors. In details, for HyCoS nanocoacervates produced at 35° C. for 5.5 h and followed by a ramp from 35° C. to 23° C. for 1.5 h (8° C./hr), at pH 4, maintain their stability until the first hour, but after this time they dissolve completely. On the contrary, at pH 7 they preserve their stability at all the different times (30 min, 1 h, 2 h, 3 h, 6 h, 8 h, 12 h, 24 h). Coacervated nanoparticles obtained by the here disclosed process do not seem to be pH sensitive and remain stable at any pH condition until 24 hours. On the contrary, coacervation occurred at room temperature produces nanoparticles that are pH-sensitive that seem to be stable at pH 7 for more than 24 hr while at pH 4 dissolve completely.

The invention claimed is:

1. A process for the preparation of coacervate nanoparticles comprising the following steps:
   a) Providing a water in oil emulsion of a biocompatible polyelectrolyte polymer selected from the group consisting of poly(L-lysine), chitosan, bovine serum albumin (BSA), human serum albumin (HSA), poly lactic-co-glycolic acid (PLGA), poly lactic-co-glycolic acid-polyethyleneglycol (PLGA-PEG) di and tri-block, poly lactic acid (PLA) and poly lactic acid-polyethyleneglycol (PLA-PEG) tri and di-block, chitosan-carboxymethyl cellulose (CMC), n-alginate and hydroxypropyl methyl cellulose (HPMC), Poly(N-isopropylacrylamide) (PNIPAAm), Poly(N-vinylcaprolactam)-hydroxyethylmethacrylate (PVCL-HEMA) grafted on dextran chain, methacrylated dextran (dex-MA), hydroxyethylmethacrylated dextran (dex-HEMA), glycidyl methacrylated dextran (dex-GMA), poly (vinylbenzyl trialkyl ammonium), poly (4-vinyl-N-alkyl-pyridinium), poly (acryloyl-oxyalkyl-trialkyl ammonium), poly (acryamidoalkyl-trialkyl ammonium), poly (diallydimethyl-ammonium), poly-(hydroxyethylmethacrylate) (poly HEMA) and maleic acid/diallylamine copolymer;
   b) Providing an aqueous solution of a biocompatible polyelectrolyte polymer having opposite charges of the polyelectrolyte polymer of step a) and selected from the group consisting of hyaluronic acid, poly(L-glutamic) acid, carrageenan, alginates, pectin, chitin, poly (styrene sulfonic acid), poly (vinyl sulfonic acid), poly (acrylic or methacrylic acid), poly (itaconic acid), maleic acid/diallylamine copolymer and chitosan;
   c) Adding two crosslinking agents, one to the emulsion and the other one to the aqueous solution;
   d) Adding a contrast agent for medical imaging either to the emulsion or the aqueous solution;
   e) Adding the aqueous solution to the emulsion at a constant temperature between 19 and 37° C. and at a pH between 3 and 7, thus obtaining the separation of the coacervate nanoparticles; and
   f) Optionally adding a further contrast agent, an optical tracer or a radiotracer for medical imaging to the coacervate nanoparticles obtained in step e).

2. A process according to claim 1, optionally continuing the coacervation at the same isothermic temperature until a complete coacervation occurs if step e) is performed at a constant temperature value in the range from 19 to 27° C.

3. A process according to claim 1, optionally rapidly cooling the emulsion to a temperature between 19 and 25° C. as soon as the coacervation starts if step e) is performed above 27° C.

4. A process according to claim 1, wherein the biocompatible polyelectrolyte polymer of step a) is chitosan, Poly Lactic-co-Glycolic Acid (PLGA) or BSA.

5. A process according to claim 1, wherein the biocompatible polyelectrolyte polymer of step b) is hyaluronic acid or chitosan.

6. A process according to claim 1, wherein the biocompatible polyelectrolyte polymer of step a) is chitosan and the biocompatible polyelectrolyte polymer of step b) is hyaluronic acid.

7. A process according to claim 1, wherein the constant temperature and pH of step e) are respectively between 22° C. and 27° C. and 3 and 7.

* * * * *